US012412667B2

(12) United States Patent
Kim et al.

(10) Patent No.: US 12,412,667 B2
(45) Date of Patent: Sep. 9, 2025

(54) NON-INVASIVE GLYCATED HEMOGLOBIN OR BLOOD GLUCOSE MEASUREMENT SYSTEM AND METHOD WHICH USE MONTE CARLO SIMULATION

(71) Applicant: KOREA I.T.S. CO., LTD., Seoul (KR)

(72) Inventors: Ki Doo Kim, Seoul (KR); Hossain Shifat, Seoul (KR)

(73) Assignee: KOREA I.T.S. CO., LTD., Seoul (KR)

( * ) Notice: Subject to any disclaimer, the term of this patent is extended or adjusted under 35 U.S.C. 154(b) by 276 days.

(21) Appl. No.: 18/577,596

(22) PCT Filed: Aug. 27, 2021

(86) PCT No.: PCT/KR2021/011504
§ 371 (c)(1),
(2) Date: Jan. 8, 2024

(87) PCT Pub. No.: WO2022/045822
PCT Pub. Date: Mar. 3, 2022

(65) Prior Publication Data
US 2024/0233961 A1    Jul. 11, 2024

(30) Foreign Application Priority Data
Aug. 27, 2020   (KR) .......................... 10-2020-0108466

(51) Int. Cl.
*G16H 50/50*   (2018.01)
*A61B 5/145*   (2006.01)
*A61B 5/1455*   (2006.01)

(52) U.S. Cl.
CPC ......... *G16H 50/50* (2018.01); *A61B 5/14532* (2013.01); *A61B 5/14546* (2013.01); *A61B 5/14551* (2013.01)

(58) Field of Classification Search
CPC ................ G16H 50/50; A61B 5/14532; A61B 5/14546; A61B 5/14551
See application file for complete search history.

(56) References Cited

U.S. PATENT DOCUMENTS

2009/0326342 A1* 12/2009 Huiku ................ A61B 5/14551
                                                              600/322
2011/0301436 A1* 12/2011 Teixeira ............. A61B 5/14552
                                                              702/19

(Continued)

FOREIGN PATENT DOCUMENTS

JP        2004-113353 A       4/2004
JP        2014-016235 A       1/2014

(Continued)

OTHER PUBLICATIONS

International Search Report issued in PCT/KR2021/011504; mailed Dec. 6, 2021.

(Continued)

*Primary Examiner* — Jason S Tiedeman
*Assistant Examiner* — Camryn B. Lewis
(74) *Attorney, Agent, or Firm* — Studebaker Brackett PLLC

(57) ABSTRACT

The present disclosure relates to a non-invasive glycated hemoglobin or blood glucose measurement system and method which use a Monte Carlo simulation, wherein the method includes: acquiring a two-dimensional scan image for a specific body part; generating a virtual three-dimensional model corresponding to the specific body part by using the two-dimensional scan image; performing a Monte Carlo simulation (MCS) on the basis of the three-dimensional model; calculating a ratio equation by collecting photoplethysmography (PPG) signals measured according to the Monte Carlo simulation; constructing a mathematical model for glycated hemoglobin or blood glucose measure- (Continued)

(a)

(b)

ment on the basis of the ratio equation; and using the mathematical model to calculate the concentration of glycated hemoglobin (HbA1c) or blood glucose and the concentration of oxygen saturation (SpO2) of a measurement subject to be measured.

12 Claims, 7 Drawing Sheets

(56) References Cited

U.S. PATENT DOCUMENTS

| | | | |
|---|---|---|---|
| 2016/0292909 A1* | 10/2016 | Lee | G06T 15/205 |
| 2017/0105663 A1* | 4/2017 | Dhawan | A61B 5/14546 |
| 2019/0139221 A1* | 5/2019 | Castro-Gonzalez | A61B 5/489 |
| 2020/0211713 A1* | 7/2020 | Shadforth | G16H 50/50 |
| 2021/0204824 A1* | 7/2021 | Wang | A61B 5/02233 |

FOREIGN PATENT DOCUMENTS

| | | |
|---|---|---|
| KR | 10-0871074 B1 | 11/2008 |
| KR | 10-2016-0028229 A | 3/2016 |
| KR | 10-2020-0029023 A | 3/2020 |

OTHER PUBLICATIONS

Written Opinion of the International Searching Authority issued in PCT/KR2021/011504; mailed Dec. 6, 2021.

* cited by examiner (a)  (b)

NON-INVASIVE GLYCATED HEMOGLOBIN OR BLOOD GLUCOSE MEASUREMENT SYSTEM AND METHOD WHICH USE MONTE CARLO SIMULATION

CROSS-REFERENCE TO RELATED APPLICATIONS

The present application is a national phase application of International Patent Application No. PCT/KR2021/011504, filed on Aug. 27, 2021, which is based upon and claims the benefit of priority to Korean Patent Application No. 10-2020-0108466, filed on Aug. 27, 2020. The disclosures of the above-listed applications are hereby incorporated by reference herein in their entirety.

TECHNICAL FIELD

The present disclosure relates to a technology for non-invasively measuring glycated hemoglobin or blood glucose, and more specifically, to a non-invasive glycated hemoglobin or blood glucose measurement system and method using a Monte Carlo simulation capable of accurately and easily measuring the concentration of glycated hemoglobin (HbA1c) or blood glucose non-invasively by performing the Monte Carlo simulation based on a virtual body part model.

BACKGROUND ART

Diabetes is a metabolic disease characterized by hyperglycemia caused by dysfunction or secretion of insulin, which is necessary for controlling blood glucose levels in the body. Chronic hyperglycemia due to diabetes causes damage and functional insufficiency in each organ of the body. In particular, the chronic hyperglycemia causes microvascular complications of the retina, kidneys, and nerves, and macrovascular complications such as arteriosclerosis, cardiovascular, and cerebrovascular diseases, resulting in an increase in mortality.

However, diabetes may reduce the worsening or complication rate of diabetes due to blood glucose control, weight loss, and medication. Accordingly, diabetic patients need to frequently measure their own blood glucose levels to manage their blood glucose levels and undergo regular glycated hemoglobin (HbA1C) tests, which are as important a treatment indicator as the blood glucose levels of the diabetic patients.

The glycated hemoglobin (HbA1c) test is a test that determines the extent to which the hemoglobin in red blood cells, which plays a role in transporting oxygen in the blood, has been glycated. Depending on the average lifespan of red blood cells, the test reflects changes in blood glucose over the past 2 to 3 months. Since glucose always exists in normal people, hemoglobin is glycated to some extent in the blood. The normal value varies depending on a test method, but usually up to 5.6% is normal.

In diabetic patients, as the concentration of glucose in the blood increases, glycated hemoglobin, in other words, the level of glycated hemoglobin, also increases. Accordingly, the direction of future treatment is decided by reviewing these results, which clearly reveal the extent of blood glucose control so far.

The conventional method of measuring glycated hemoglobin (HbA1c) is to acquire a capillary blood sample by collecting blood from a vein in the arm of a measurement subject to be measured measurement subject or pricking the tip of the finger with a small and pointed needle, and use the acquired blood to measure the concentration of glycated hemoglobin (HbA1c). The invasive method of measuring glycated hemoglobin has an issue of increasing the burden of blood collection on measurement subjects to be measured and providing inaccurate levels in cases of short red blood cell lifespan, pregnancy, or kidney disease.

RELATED ART DOCUMENT

Patent Document

Korean Patent No. 10-0871074 (Nov. 24, 2008)

DETAILED DESCRIPTION OF INVENTION

Technical Problem

A technical task of the present disclosure is directed to providing a non-invasive glycated hemoglobin or blood glucose measurement system and method using a Monte Carlo simulation capable of accurately and easily measuring the concentration of glycated hemoglobin (HbA1c) or blood glucose non-invasively by performing the Monte Carlo simulation based on a virtual body part model.

Technical Solution

In an embodiment, a non-invasive glycated hemoglobin or blood glucose measurement method which uses a Monte Carlo simulation includes: acquiring a two-dimensional scan image for a specific body part; generating a virtual three-dimensional model corresponding to the specific body part by using the two-dimensional scan image; performing the Monte Carlo simulation (MCS) on the basis of the three-dimensional model; calculating a ratio equation by collecting photoplethysmography (PPG) signals measured according to the Monte Carlo simulation; constructing a mathematical model for glycated hemoglobin or blood glucose measurement on the basis of the ratio equation; and using the mathematical model to calculate a concentration of glycated hemoglobin (HbA1c) or blood glucose and the concentration of oxygen saturation (SpO2) of a measurement subject to be measured.

The two-dimensional scan image may include either an MRI image or a CT image for the specific body part.

The specific body part may include a part where capillaries existing under the skin are able to be sensed depending on a thickness of the skin.

The mathematical model may include a mathematical model based on machine learning.

The generation of the three-dimensional model may include generating the three-dimensional model by applying a 3D conversion algorithm to the two-dimensional scan image.

The performance of the Monte Carlo simulation may include: irradiating virtual first to third incident lights having different wavelength values toward the three-dimensional model through virtual first to third LED modules positioned on one side of the three-dimensional model; and detecting virtual first to third derived lights derived from the first to third incident lights via the three-dimensional model through a virtual light detection unit positioned corresponding to the first to third LED modules.

The light detection unit may be positioned at an opposite side or on the same side surface relative to positions of the first to third LED modules.

The performance of the Monte Carlo simulation may include simulating each movement of the incident light and the derived light as a result of applying Monte Carlo rules to virtual photons.

The Monte Carlo rule may include a traversing rule regarding at least one of reflection, transmission, or absorption according to collision between a specific photon and a specific medium.

The calculation of the ratio equation may include calculating ratio equations for different wavelength values based on amplitude of the photoplethysmography (PPG) signals.

The calculation of the ratio equation may include applying each derived light of first and second derived light sets composed of two of the first to third derived lights to the ratio equation regarding the different wavelength values to generate first and second ratio equations.

The construction of the mathematical model may include constructing a mathematical model between a value of the ratio equation and each value of glycated hemoglobin (HbA1c) or blood glucose and oxidation saturation (SpO2) predefined corresponding to a reference photoplethysmography signal.

The construction of the mathematical model may include constructing a mathematical model between values of each of the first and second ratio equations and each value of glycated hemoglobin (HbA1c) or blood glucose and oxidation saturation (SpO2) predefined.

The construction of the mathematical model may include calibrating the mathematical model based on actual values of the glycated hemoglobin (HbA1c) or blood glucose and the oxidation saturation (SpO2) measured from the measurement subject to be measured.

In an embodiment, a non-invasive glycated hemoglobin or blood glucose measurement system which uses a Monte Carlo simulation includes: a 3D modeling unit that acquires a two-dimensional scan image for a specific body part to generate a virtual three-dimensional model; a simulation performance unit that performs the Monte Carlo simulation (MCS) on the basis of the three-dimensional model; a measurement model construction unit that calculates a ratio equation by collecting photoplethysmography (PPG) signals measured according to the Monte Carlo simulation to construct a mathematical model for glycated hemoglobin or blood glucose measurement on the basis of the ratio equation; and a concentration calculation unit that uses the mathematical model to calculate a concentration of glycated hemoglobin (HbA1c) or blood glucose and the concentration of oxygen saturation (SpO2) of a measurement subject to be measured.

Effects of the Invention

The disclosed technology may have the following effects. However, it does not mean that a specific exemplary embodiment should include the entire following effects or should include only the following effects, and it should not be understood that the scope of right of disclosed technology is limited thereto.

A non-invasive glycated hemoglobin or blood glucose measurement system and method using a Monte Carlo simulation according to an embodiment of the present disclosure can accurately and easily measure the concentration of glycated hemoglobin (HbA1c) or blood glucose non-invasively by performing the Monte Carlo simulation based on a virtual body part model.

BEST MODE FOR CARRYING OUT THE INVENTION

Figure 1:
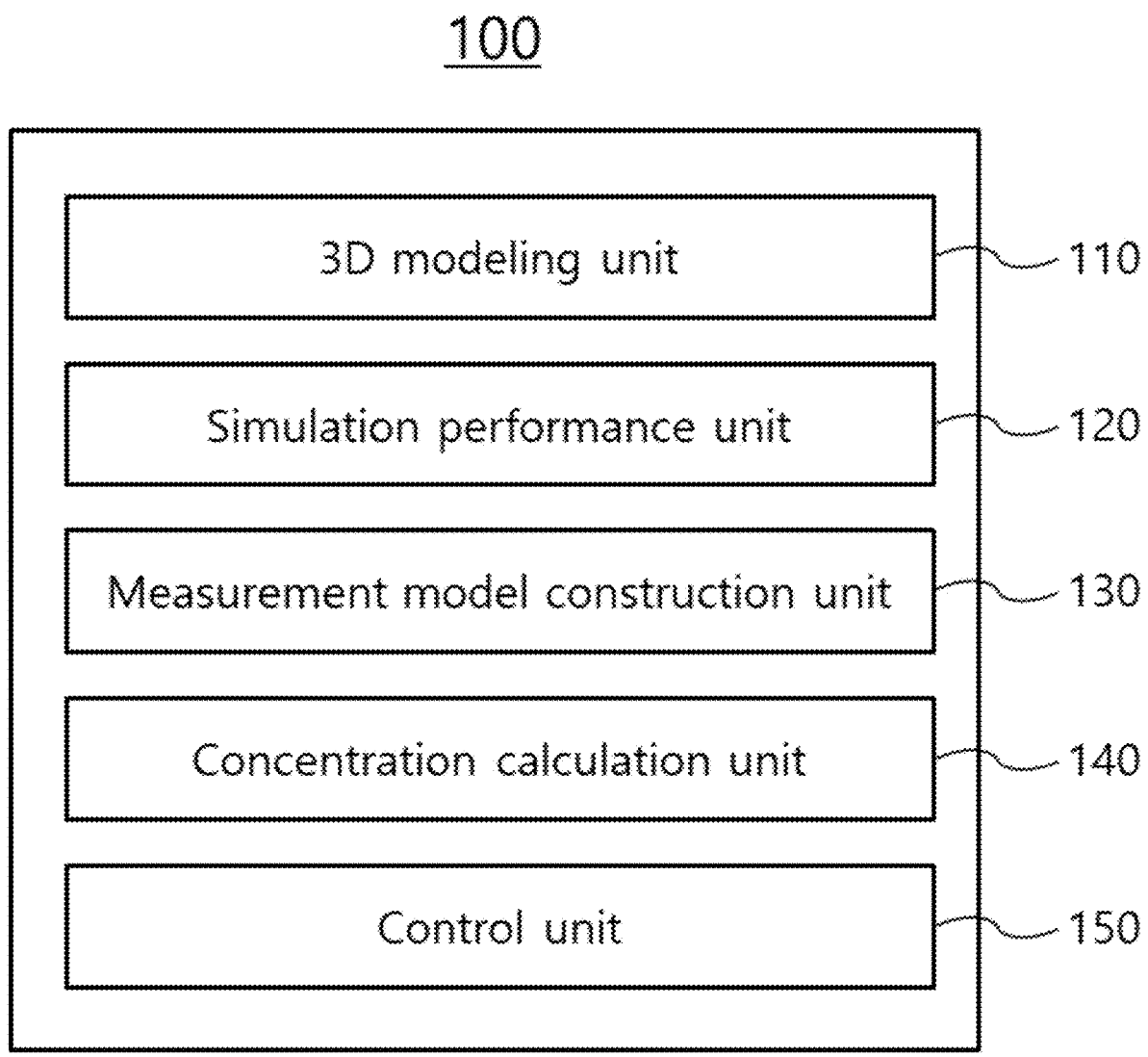
FIG. 1 is a configuration diagram illustrating a non-invasive glycated hemoglobin or blood glucose measurement system according to an embodiment of the present disclosure.

The explanation of the present disclosure is merely an embodiment for structural or functional explanation, so the scope of the present disclosure should not be construed to be limited to the embodiments explained in the embodiment. That is, since the embodiments may be implemented in several forms without departing from the characteristics thereof, it should also be understood that the described embodiments are not limited by any of the details of the foregoing description, unless otherwise specified, but rather should be construed broadly within its scope as defined in the appended claims. Therefore, various changes and modifications that fall within the scope of the claims, or equivalents of such scope are therefore intended to be embraced by the appended claims.

Terms described in the present disclosure may be understood as follows.

While terms such as "first", "second", etc., may be used to describe various components, such components must not be understood as being limited to the above terms. The above terms are used to distinguish one component from another. For example, a first component may be referred to as a second component without departing from the scope of rights of the present disclosure, and likewise a second component may be referred to as a first component.

It will be understood that when an element is referred to as being "connected to" another element, it may be directly connected to the other element or intervening elements may also be present. In contrast, when an element is referred to as being "directly connected to" another element, no intervening elements are present. In addition, unless explicitly described to the contrary, the word "comprise" and variations such as "comprises" or "comprising" will be understood to imply the inclusion of stated elements but not the exclusion of any other elements. Meanwhile, other expressions describing relationships between components such as "between", "immediately between" or "adjacent to" and "directly adjacent to" may be construed similarly.

Singular forms "a", "an" and "the" in the present disclosure are intended to include the plural forms as well, unless the context clearly indicates otherwise. It will be further understood that terms such as "including" or "having", etc., are intended to indicate the existence of the features, numbers, operations, actions, components, parts, or combinations thereof disclosed in the specification, and are not intended to preclude the possibility that one or more other features, numbers, operations, actions, components, parts, or combinations thereof may exist or may be added.

In each phase, reference numerals (for example, a, b, c, etc.) are used for the sake of convenience in description, and such reference numerals do not describe the order of each phase. The order of each phase may vary from the specified order, unless the context clearly indicates a specific order. In other words, each phase may take place in the same order as the specified order, may be performed substantially simultaneously, or may be performed in a reverse order.

The present disclosure may be implemented as machine-readable codes on a machine-readable medium. The machine-readable medium may include any type of recording device for storing machine-readable data. Examples of the machine-readable recording medium may include a read-only memory (ROM), a random access memory (RAM), a compact disk-read only memory (CD-ROM), a magnetic tape, a floppy disk, optical data storage, or any other appropriate type of machine-readable recording medium. The medium may also be carrier waves (for example, Internet transmission). The computer-readable recording medium may be distributed among networked machine systems which store and execute machine-readable codes in a de-centralized manner.

The terms used in the present application are merely used to describe particular embodiments, and are not intended to limit the present disclosure. Unless otherwise defined, all terms used herein, including technical or scientific terms, have the same meanings as those generally understood by those with ordinary knowledge in the field of art to which the present disclosure belongs. Such terms as those defined in a generally used dictionary are to be interpreted to have the meanings equal to the contextual meanings in the relevant field of art, and are not to be interpreted to have ideal or excessively formal meanings unless clearly defined in the present application.

FIG. 1 is a configuration diagram illustrating a non-invasive glycated hemoglobin or blood glucose measurement system according to an embodiment of the present disclosure.

Referring to FIG. 1, a non-invasive glycated hemoglobin or blood glucose measurement system 100 may include a 3D modeling unit 110, a simulation performance unit 120, a measurement model construction unit 130, a concentration calculation unit 140, and a control unit 140.

The 3D modeling unit 110 may acquire a two-dimensional scan image of a specific body part and generate a virtual three-dimensional model. Herein, the specific body part may include a part where capillaries existing under the skin may be sensed depending on a thickness of the skin. For example, the specific body part may include fingers, wrist, forehead, cheek, ear, etc., but is not necessarily limited thereto, and may include various body parts depending on installation conditions.

In addition, the two-dimensional scan image may include either an MRI image or a CT image for a specific body part. For example, the 3D modeling unit 110 may generate a virtual three-dimensional model of the finger by applying a 3D conversion algorithm to MRI images of the finger. The non-invasive glycated hemoglobin or blood glucose measurement system 100 may provide an effective method of non-invasively measuring glycated hemoglobin or blood glucose by performing a Monte Carlo simulation based on a virtual finger model.

The simulation performance unit 120 may perform the Monte Carlo Simulation (MCS) based on a three-dimensional model. Herein, the Monte Carlo Simulation (MCS) may correspond to simulation based on Monte Carlo methods and experiments.

In this connection, Monte Carlo methods and experiments may correspond to a broad calculation class of computational algorithms that rely on repeated random sampling to obtain numerical results. The basic concept is to use randomness to solve problems that are in principle deterministic, and the method may be very useful in solving physics and mathematics problems where other approaches are difficult or impossible to use. In addition, the Monte Carlo methods may be mainly used in three classes of problems of a winner drawing: optimization, numerical integration, and probability distributions.

In principle, Monte Carlo methods may be used to solve any problem that requires a probabilistic analysis. For infinitely large numbers, the integral calculus described by the expected value of any random variable may be approximated by the empirical mean of independent samples of the variable (in other words, the sample mean). Mathematicians may use a Markov chain Monte Carlo (MCMC) sampler when the probability distribution of the variables is parameterized. In this connection, the main idea is to design an appropriate Markov chain model with a prescribed fixed probability distribution. In other words, in the limit, the samples generated by the MCMC method may correspond to samples from the desired (target) distribution. By ergodic theory, the time-invariant distribution may be approximated by empirical measurements of the random states of the MCMC sampler.

In addition, the simulation performance unit 120 may perform the Monte Carlo simulation based on an actual human skin model or an entire model of limbs (for example, wrist, fingers, earlobe, etc.). In this connection, an MRI image (or CT image) may be used, and MRI image slices may be used to construct a three-dimensional physical model of a specific body part. The model may be configured of bones, muscles, ligaments, tendons, veins, arteries, fat, and skin layers; arteries, veins, and skin capillaries may contain blood; and blood may be configured of HHb, HbO, and HbA1c hemoglobin cells.

On average, the thickness of the skin layer may be 0.95 mm and may include six layers. For example, the six layers may include stratum corneum, epidermis, papillary dermis, upper blood net dermis, reticular dermis, and deep blood net dermis. In addition, there may be a fat layer next to the skin layer of the model, followed by muscles, bones, and other elements on the MRI image.

In addition, the simulation performance unit 120 may perform the Monte Carlo simulation under the condition that the LED transmitter and photon receiver are installed at a specific location in the 3D model. In other words, the Monte Carlo simulation may virtually materialize the movement of virtual photons emitted from a virtual LED, that is, reflection, transmission, or absorption according to interaction with a virtual three-dimensional model.

In this connection, virtual photons are assumed to move according to Monte Carlo rules, and the movement of virtual photons may correspond to the movement of virtual incident light and derived light. Herein, the Monte Carlo rule may include a traversing rule regarding at least one of reflection, transmission, or absorption according to collision between a specific photon and a specific medium. The Monte Carlo rule is explained in more detail in FIG. 6.

The measurement model construction unit 130 may collect photoplethysmography (PPG) signals measured according to the Monte Carlo simulation, calculate a ratio equation, and construct a mathematical model for measuring glycated hemoglobin or blood glucose based on the ratio equation. The measurement model construction unit 130 may acquire the photoplethysmography (PPG) signals measured in the virtual PD as a result of the Monte Carlo simulation from the simulation performance unit 120, and based thereon, construct a mathematical model for measuring glycated hemoglobin or blood glucose. In an embodiment, the mathematical model may correspond to a mathematical model based on machine learning.

The blood volume in arteries, veins, and capillaries may be updated according to the ideal photoplethysmography (PPG) signals, and the blood may also include predefined values of oxygen saturation (SpO2), glycated hemoglobin (HbA1c), or blood glucose. The measurement model construction unit 130 may calculate the AC-DC ratio equation based on the amplitude of the collected photoplethysmography (PPG) signals, and may be expressed as Equation 1 below.

$$R = \frac{\left(\frac{\Delta I}{I}\right)_{\lambda_1}}{\left(\frac{\Delta I}{I}\right)_{\lambda_2}}$$ [Equation 1]

In the equation above, R represents the ratio equation, $\Delta I$ represents the difference value of light intensity between a peak value and a valley value of the PPG signal, I represents the intensity of derived light, and $\lambda_1$ and $\lambda_2$ represent different wavelength values. In other words, the measurement model construction unit 130 may derive ratio equations for different wavelength values based on the amplitude of the photoplethysmography (PPG) signals measured according to the Monte Carlo simulation.

In an embodiment, the measurement model construction unit 130 may construct a mathematical model between predefined values of glycated hemoglobin (HbA1c) or blood glucose and oxidative saturation (SpO2) by corresponding the value of the ratio equation to the reference photoplethysmography signal. Herein, the reference photoplethysmography (PPG) signal may correspond to an ideal photoplethysmography signal. The blood volume in arteries, veins and capillaries may be updated according to the ideal photoplethysmography (PPG) signal, and the blood may also contain predefined values of oxygen saturation (SpO2) or blood glucose and glycated hemoglobin (HbA1c). Using this, the measurement model construction unit 130 may specify the relationship between the ratio equation derived through the Monte Carlo simulation and each value of glycated hemoglobin (HbA1c) or blood glucose and oxidation saturation (SpO2) into a mathematical model.

In an embodiment, the measurement model construction unit 130 may calibrate a mathematical model based on actual values of glycated hemoglobin (HbA1c) or blood glucose and oxygen saturation (SpO2) measured from a measurement subject to be measured. The measurement model construction unit 130 may improve the prediction accuracy of the mathematical model by calibrating the mathematical model constructed through simulation using actual values measured by humans. The calibration of the mathematical model may be performed to reduce the difference between actual and predicted values.

The concentration calculation unit 140 may calculate the concentration of glycated hemoglobin (HbA1c) or blood glucose and oxidation saturation (SpO2) of the measurement subject to be measured using a mathematical model. In other words, the concentration calculation unit 140 may apply a previously constructed mathematical model to the actual value measured from the measurement subject to be measured to non-invasively and highly accurately predict the concentration of glycated hemoglobin (HbA1c) or blood glucose and oxidation saturation (SpO2) of the measurement subject to be measured.

The control unit 140 may control the overall operation of the non-invasive glycated hemoglobin or blood glucose measurement system 100 and manage the control flow or data flow among the 3D modeling unit 110, the simulation performance unit 120, the measurement model construction unit 130, and the concentration calculation unit 140.

Figure 2:
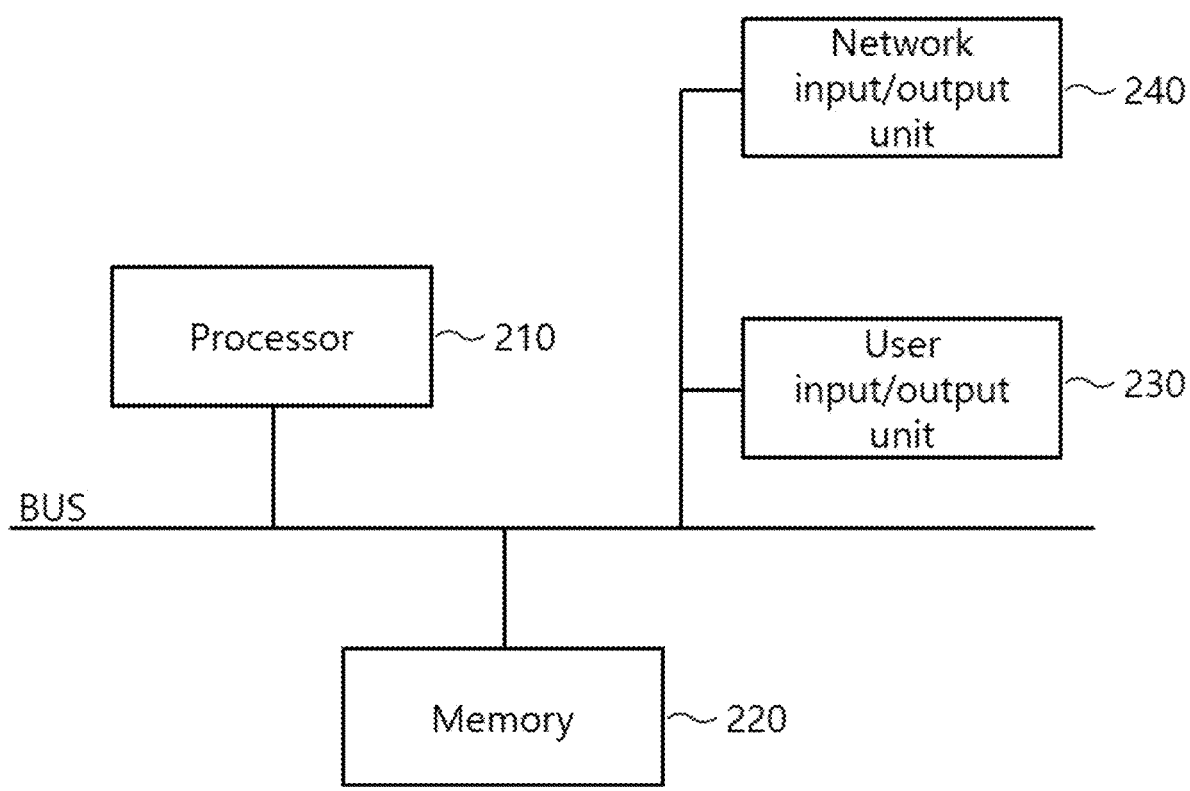
FIG. 2 is a diagram illustrating a system configuration of the non-invasive glycated hemoglobin or blood glucose measurement system.

FIG. 2 is a diagram illustrating a system configuration of the non-invasive glycated hemoglobin or blood glucose measurement system.

Referring to FIG. 2, the non-invasive glycated hemoglobin or blood glucose measurement system 100 may be implemented including a processor 210, a memory 220, a user input/output unit 230, and a network input/output unit 240.

The processor 210 may execute a procedure that processes each stage in the process of operating the non-invasive glycated hemoglobin or blood glucose measurement system 100, and may manage the memory 220 that is read or written throughout the process. In addition, the synchronization time between a volatile memory and a non-volatile memory in the memory 220 may be scheduled. The processor 210 may control the overall operation of the non-invasive glycated hemoglobin or blood glucose measurement system 100, and may be electrically connected to the memory 220, the user input/output unit 230, and the network input/output unit 240 to control data flow therebetween. The processor 210 may be implemented as a central processing unit (CPU) of the non-invasive glycated hemoglobin or blood glucose measurement system 100.

The memory 220 may be implemented as a non-volatile memory such as a solid state drive (SSD) or a hard disk drive (HDD), and may include an auxiliary memory used to store all data required for the non-invasive glycated hemoglobin or blood glucose measurement system 100 and a main memory unit implemented as a volatile memory such as random access memory (RAM).

The user input/output unit 230 may include an environment for receiving user input and an environment for outputting specific information to a user. For example, the user input/output unit 230 may include an input device including an adapter such as a touch pad, a touch screen, an on-screen keyboard, or a pointing device, and an output device including an adapter such as a monitor or a touch screen. In an embodiment, the user input/output unit 230 may correspond to a computing device connected via remote access. In this connection, the non-invasive glycated hemoglobin or blood glucose measurement system 100 may be performed as a server.

The network input/output unit 240 may include an environment for connecting with an external device or a system through a network, and may include an adapter for communication, for example, a local area network (LAN), a metropolitan area network (MAN), a wide area network (WAN), a value added network (VAN), and the like.

Figure 3:
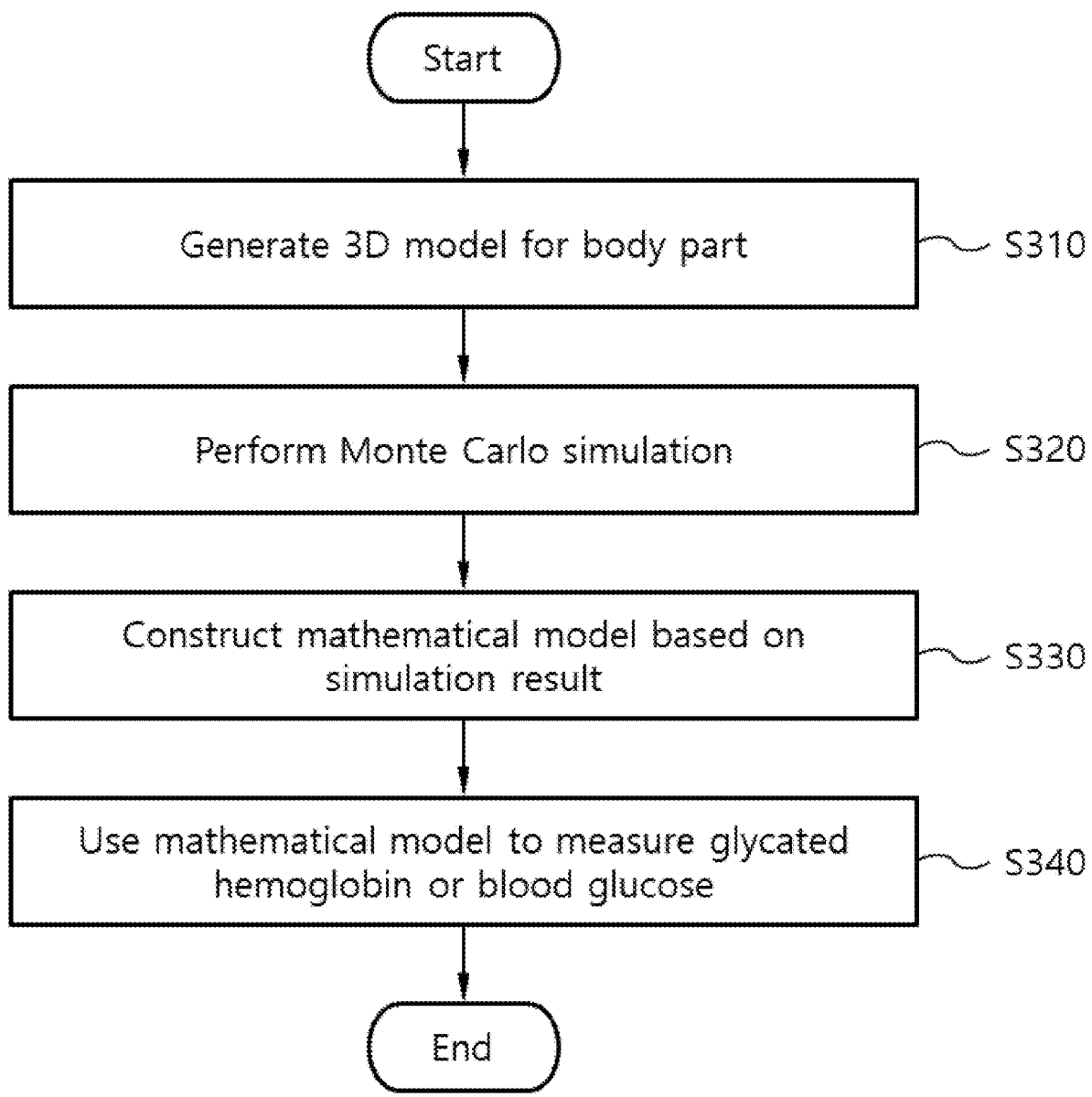
FIG. 3 is a flowchart for explaining a method of measuring glycated hemoglobin or blood glucose according to an embodiment of the present disclosure.

FIG. 3 is a flowchart for explaining a method of measuring glycated hemoglobin or blood glucose according to an embodiment of the present disclosure.

Referring to FIG. 3, the non-invasive glycated hemoglobin or blood glucose measurement system 100 may generate a virtual three-dimensional model by acquiring a two-dimensional scan image of a specific body part through the 3D modeling unit 110 (stage S310). The non-invasive glycated hemoglobin or blood glucose measurement system 100 may perform the Monte Carlo simulation (MCS) based on a three-dimensional model through the simulation performance unit 120 (stage S320).

In addition, the non-invasive glycated hemoglobin or blood glucose measurement system 100 may collect photoplethysmography (PPG) signals measured according to the Monte Carlo simulation through the measurement model construction unit 130 to calculate a ratio equation and construct a mathematical model for measuring glycated hemoglobin or blood glucose (stage S330). The non-invasive glycated hemoglobin or blood glucose measurement system 100 may non-invasively calculate the concentration of glycated hemoglobin (HbA1c) or blood glucose and oxidation saturation (SpO2) of the measurement subject to be measured using a mathematical model through the concentration calculation unit 140 (stage S340).

Figure 4:
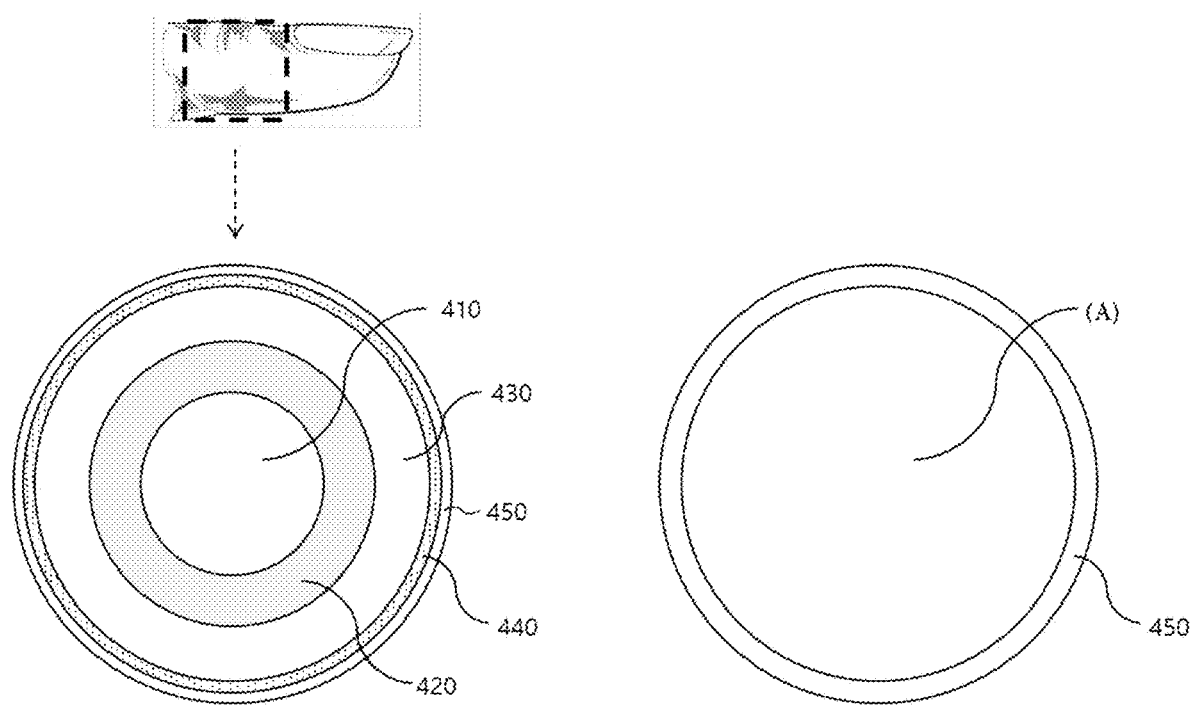
FIG. 4 is an example diagram illustrating anatomical features of a tissue model for a finger.

FIG. 4 is an example diagram illustrating anatomical features of a tissue model for a finger.

Referring to FIG. 4, the non-invasive glycated hemoglobin or blood glucose measurement system 100 may construct a virtual three-dimensional model for a specific body part through the 3D modeling unit 110. The finger model constructed by the 3D modeling unit 110 may be configured of each layer of skin 450, fat 440, and muscle 430 from the outside, and the muscle 430 may include ligaments, tendons 420, and bones 410 therein. In addition, in the finger model, the configurations below the skin 450 may be expressed by modeling (A) using MRI images or CT images.

The skin 450 may be configured of six sublayers. In other words, the skin 450 may include the stratum corneum, epidermis, papillary dermis, upper blood net dermis, reticular dermis, and deep blood net dermis.

In addition, each of the sublayers configuring the skin 450 may include parameters related to thickness (t), blood volume ($V_b$), and moisture content ($V_w$) for the Monte Carlo simulation, and may be set as shown in Table 1 below, as an example.

TABLE 1

| Dermal Sublayer | t(mm) | $V_b$ | $V_w$ |
|---|---|---|---|
| Stratum corneum | 0.02 | 0 | 0.05 |
| Epidermis | 0.25 | 0 | 0.2 |
| Papillary dermis | 0.1 | 0.04 | 0.5 |
| Upper blood net dermis | 0.08 | 0.3 | 0.6 |
| Reticular dermis | 0.2 | 0.04 | 0.7 |
| Deep blood net dermis | 0.3 | 0.1 | 0.7 |

In addition, the finger model may include optical parameters that affect light propagation through tissue for the Monte Carlo simulation. For example, the finger model may include the absorption coefficient and scattering coefficient for each wavelength as optical parameters for skin, fat, muscle, bone, oxyhemoglobin, deoxyhemoglobin, and water, respectively.

Figure 5:
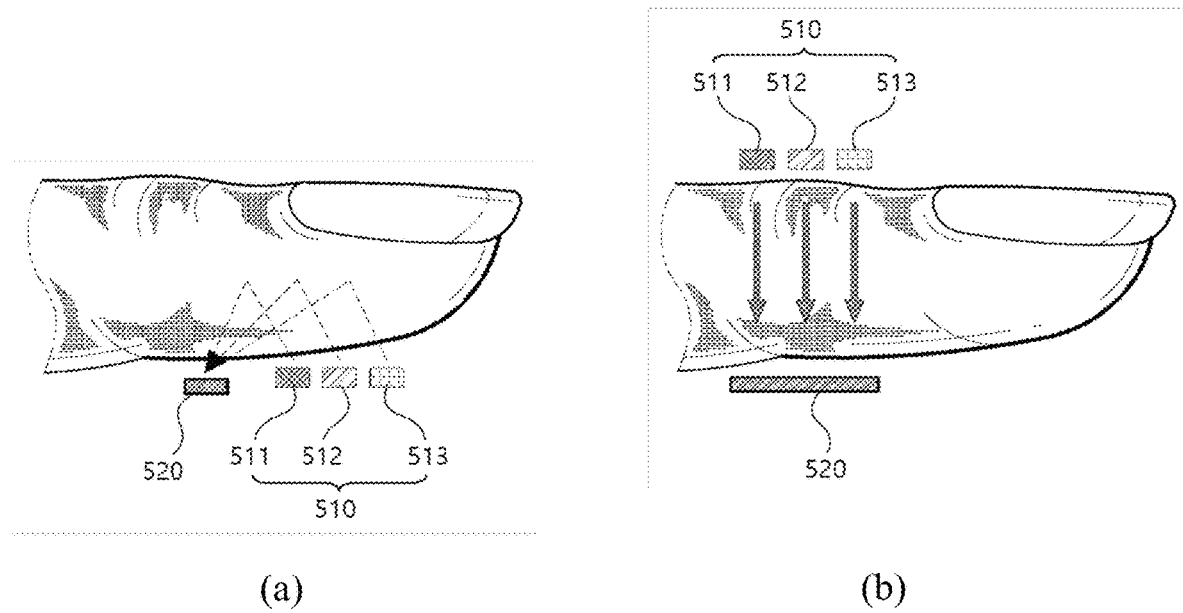
FIG. 5 is an example diagram illustrating an LED transmitter and receiver applied to a Monte Carlo simulation.

FIG. 5 is an example diagram illustrating an LED transmitter and receiver applied to the Monte Carlo simulation.

Referring to FIG. 5, the Monte Carlo simulation performed in the non-invasive glycated hemoglobin or blood glucose measurement system 100 may be performed based on a three-dimensional model generated by the 3D modeling unit 110. In addition, the Monte Carlo simulation may be performed based on an LED transmitter and photon receiver fixedly disposed on one side of the three-dimensional model.

In an embodiment, the Monte Carlo simulation performed by the simulation performance unit 120 may be performed by including the processes of radiating virtual first to third incident lights having different wavelength values toward the three-dimensional model through virtual first to third LED modules 511 to 513 positioned on one side of the three-dimensional model, and sensing virtual first to third derived lights derived from the first to third incident lights via the three-dimensional model through a virtual light detection unit 520 positioned corresponding to the first to third LED modules 511 to 513. In this connection, the first to third LED modules 511 to 513 may correspond to an LED transmitter, and the light detection unit 520 may correspond to a photon receiver.

In this connection, the light detection unit 520 may be positioned at an opposite point as shown in (b) or on the same side surface as shown in (a) based on the positions of the first to third LED modules 511 to 513. The wavelength values of the first to third LED modules 511 to 513 may be set differently. For example, the first LED module 511 may be set to emit green light, the second LED module 512 may be set to emit red light, and the third LED module 513 may be set to emit infrared (IR) light. In other words, the first LED module 511 may have a first wavelength value ($\lambda_1$), the second LED module 512 may have a second wavelength value ($\lambda_2$), and the third LED module 513 may have a third wavelength value ($\lambda_3$).

As a result, the simulation performance unit 120 may perform the Monte Carlo simulation of the movement of virtual photons based on a virtual three-dimensional model corresponding to a specific body part and a virtual LED module 510 and light detection unit 520 that are fixedly disposed based on the three-dimensional model. In this connection, virtual photons may be randomly generated by applying the physical limits of the LED, and the movement of virtual photons may be defined according to Monte Carlo rules, which will be described in more detail based on FIG. 6 below.

Figure 6:
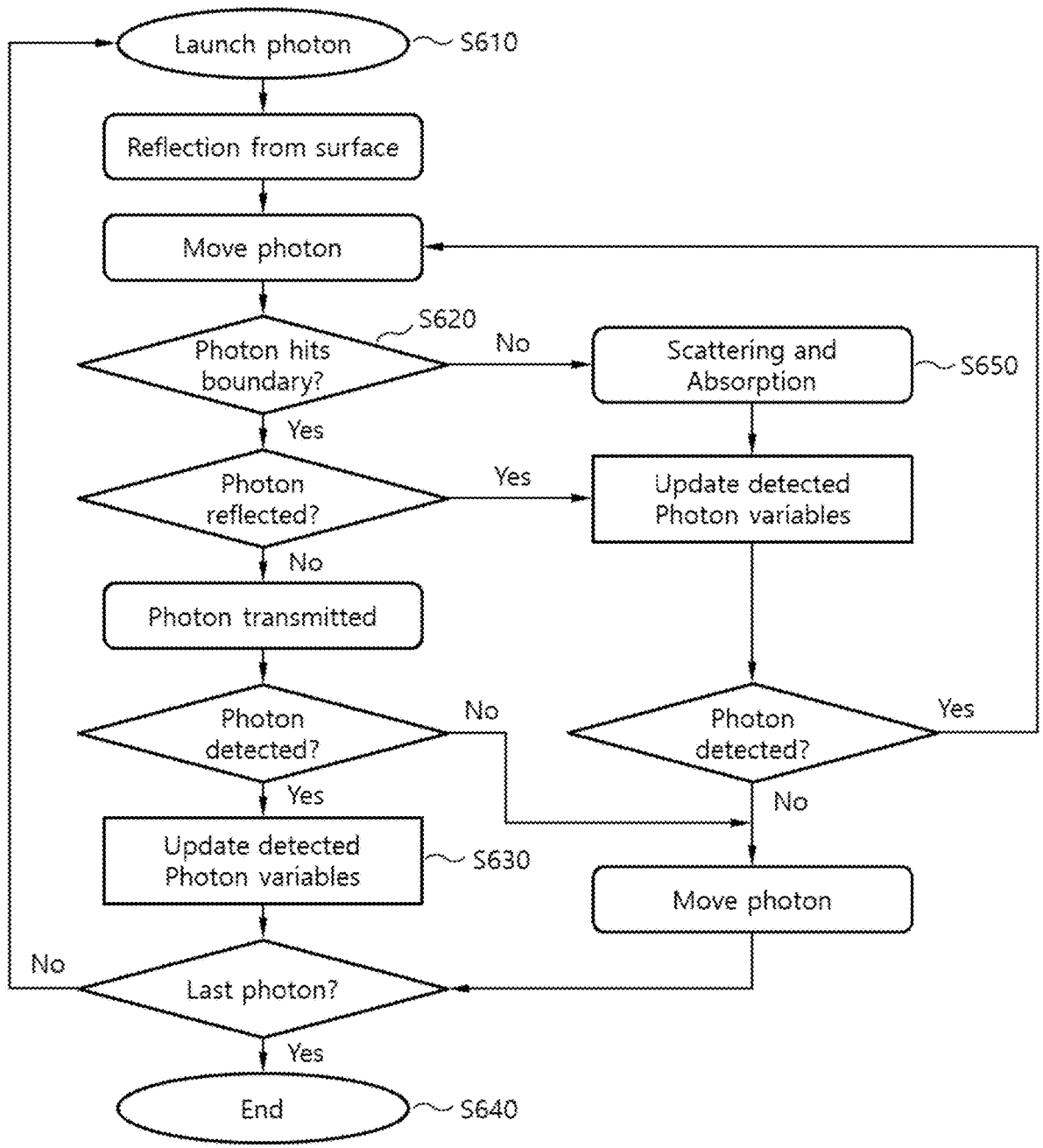
FIG. 6 is a flowchart for explaining the traversing rule of a photon projected through the Monte Carlo simulation.

FIG. 6 is a flowchart for explaining the traversing rule of a photon projected through the Monte Carlo simulation.

Referring to FIG. 6, the Monte Carlo simulation may determine the movement of each virtual photon according to Monte Carlo rules. Herein, the Monte Carlo rule may correspond to a traversing rule that defines the movement of virtual photons. In other words, each of the virtual photons may be reflected, transmitted, or absorbed by collision with the medium, and each event may cause a change in at least one of position, direction, or weight.

More specifically, through the Monte Carlo simulation, virtual photons (photon packets) with initial direction and position coordinates may be emitted toward the tissue surface (S610). In this connection, the initial statistical weight of the photon packet may be set to 1 (in other words, w=1).

After initial correction for reflection from the tissue surface, photon packets may propagate according to the unit size (l) calculated by random sampling of the probability of photon scattering, and the unit size (l) may be expressed as Equation 2 below:

$$l = -\frac{\ln(\xi)}{\mu_s} \quad \text{[Equation 2]}$$

In the equation above, $\xi(0<\xi<1)$ represents a pseudo random number generated by a computer, and $\mu_s$ represents the scattering coefficient.

When the photon packet reaches the boundary, a determination may be made as to whether it will be reflected inward or transmitted (S620). When a photon is transmitted, it may be determined whether it falls below the detection standard by the light detection unit. When a photon is detected by the light detection unit, numerical values for predefined variables, in other words, optical path, detected intensity, and penetration depth, may be determined (S630), and propagation of the corresponding photon packet may be terminated (S640).

In addition, when photons freely propagate, absorption and scattering events may occur (S650). In other words, a part of the photon weight may be absorbed in the medium and the remaining weight may continue to propagate, and the absorbed weight (Aw) may be expressed as Equation 3 below.

$$\Delta w = \frac{\mu_a}{\mu_a + \mu_s} \cdot w \quad \text{[Equation 3]}$$

In the equation above, $\mu_a$ represents the absorption coefficient and w represents the weight of the photon.

In addition, for photon scattering, the direction of the photon packet may be determined by a randomly generated deflection angle and azimuthal angle. Specifically, the scattering angle $\theta$ may be calculated using Equation 4 below.

$$\theta = \cos^{-1}\frac{1}{2g}\left[1 + g^2 - \left(\frac{1-g^2}{1-g+2g\xi}\right)^2\right] \quad \text{[Equation 4]}$$

In the equation above, g represents a variable related to symmetry. In other words, in the case of g=0, it may correspond to isotropy, and in the case of g=+1, it may correspond to anisotropy with a positive direction.

In addition, the azimuth angle $\phi$ may be randomly generated between 0 and $27\pi$ and may be expressed as Equation 5 below.

$$\phi = 2\pi\xi \quad \text{[Equation 5]}$$

Afterwards, the Monte Carlo simulation may repeatedly perform the same process until the photon packet is detected or discarded. When the weight of the photon is too small or it propagates without being detected by the light detection unit, the photon may be discarded and a new photon packet may be generated and emitted. The Monte Carlo simulation may repeatedly perform the process until a desired number of photon packets are detected in the light detection unit.

Figure 7:
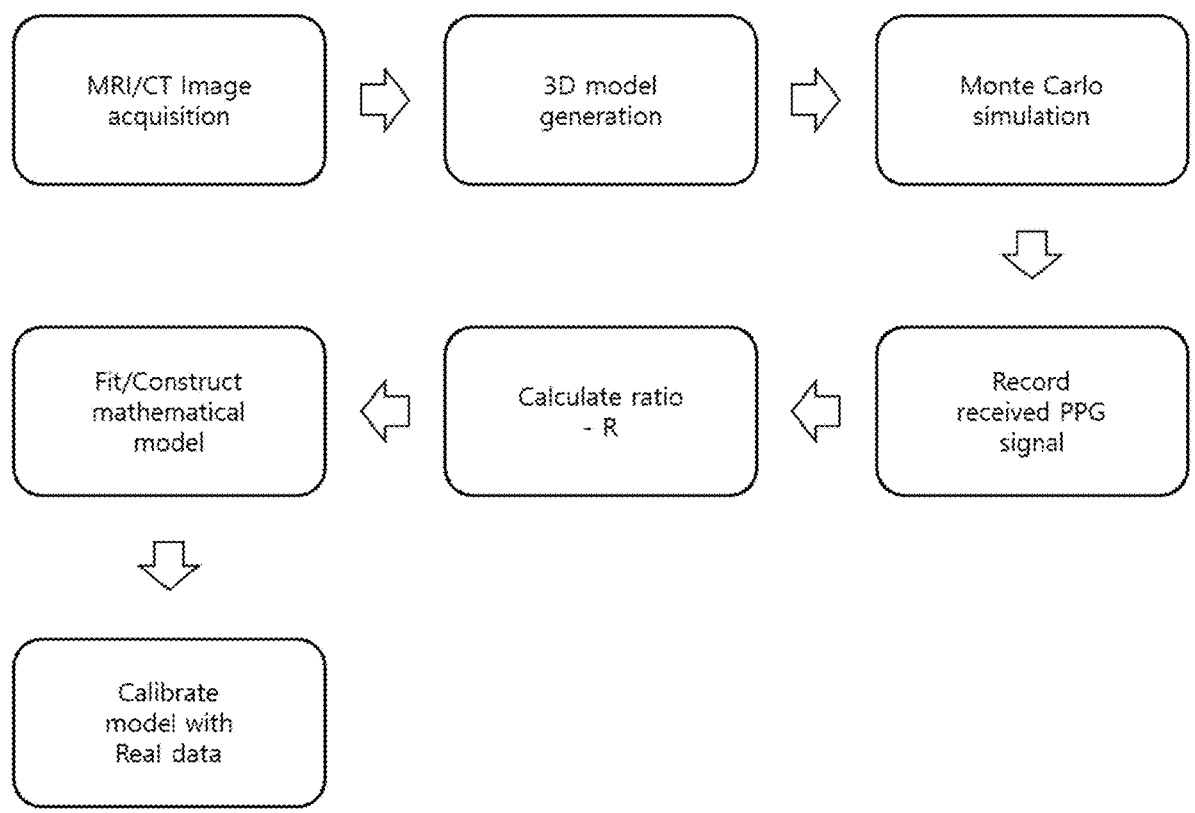
FIG. 7 is a diagram illustrating a process for estimating the concentration of glycated hemoglobin or blood glucose using the Monte Carlo simulation according to an embodiment of the present disclosure.

FIG. 7 is a diagram illustrating a process for estimating the concentration of glycated hemoglobin or blood glucose using the Monte Carlo simulation according to an embodiment of the present disclosure.

Referring to FIG. 7, the non-invasive glycated hemoglobin or blood glucose measurement system 100 may generate a measurement model for measuring glycated hemoglobin or blood glucose through the Monte Carlo simulation. Specifically, the non-invasive glycated hemoglobin or blood glucose measurement system 100 may generate a 3D model of a body part based on MRI/CT images, and collect PPG signals by performing the Monte Carlo simulation based on the 3D model.

In addition, the non-invasive glycated hemoglobin or blood glucose measurement system 100 may generate a ratio equation based on the PPG signal, and based thereon, construct a mathematical model of the ratio equation and the relationship between the concentration of oxidative saturation (SpO2) and the concentration of glycated hemoglobin (HbA1c) or blood glucose. In this connection, the mathematical model may be calibrated in a way to minimize the difference between the actual value and the predicted value, and the non-invasive glycated hemoglobin or blood glucose measurement system 100 may calculate the concentration of glycated hemoglobin (HbA1c) or blood glucose and oxidation saturation (SpO2) of the measurement subject to be measured using the calibrated mathematical model.

In an embodiment, the non-invasive glycated hemoglobin or blood glucose measurement system 100 may apply each derived light of first and second derived light sets composed of two of the first to third derived lights to the ratio equation regarding the different wavelength values to generate first and second ratio equations.

For example, when the first derived light set includes a second wavelength ($\lambda_2$) and a third wavelength ($\lambda_3$), the non-invasive glycated hemoglobin or blood glucose measurement system 100 may substitute a second wavelength ($\lambda_2$) and a third wavelength ($\lambda_3$) into Equation 1 above to acquire a first ratio equation $R_1$ as shown in Equation 6 below.

$$R_1 = \frac{\left(\frac{\Delta I}{I}\right)_{\lambda_2}}{\left(\frac{\Delta I}{I}\right)_{\lambda_3}} \quad \text{[Equation 6]}$$

In the equation above, $$\left(\frac{\Delta I}{I}\right)_{\lambda_2}$$

represents the transmittance (or reflectance) when irradiated with the second LED having the second wavelength ($\lambda_2$), and $$\left(\frac{\Delta I}{I}\right)_{\lambda_3}$$

represents the transmittance (or reflectance) when irradiated with the third LED having the third wavelength ($\lambda_3$).

In addition, when the second derived light set includes a first wavelength ($\lambda_1$) and a third wavelength ($\lambda_3$), the non-invasive glycated hemoglobin or blood glucose measurement system 100 may substitute a first wavelength ($\lambda_1$) and a third wavelength ($\lambda_3$) into Equation 1 above to acquire a second ratio equation $R_2$ as shown in Equation 7 below.

$$R_2 = \frac{\left(\frac{\Delta I}{I}\right)_{\lambda_1}}{\left(\frac{\Delta I}{I}\right)_{\lambda_3}} \qquad \text{[Equation 7]}$$

In the equation above, $$\left(\frac{\Delta I}{I}\right)_{\lambda_1}$$

represents the transmittance (or reflectance) when irradiated with the first LED having the first wavelength ($\lambda_1$).

In an embodiment, the non-invasive glycated hemoglobin or blood glucose measurement system 100 may construct a mathematical model between the values of each of the first and second ratio equations and each of the predefined values of glycated hemoglobin (HbA1c) and oxidation saturation (SpO2), which may be expressed as Equations 8 and 9 below, respectively.

$$\% \, S_p O2 = f_1(R_1, R_2) \qquad \text{[Equation 8]}$$

$$\% \, H_b A1c = f_2(R_1, R_2) \qquad \text{[Equation 9]}$$

In the equation above, % SpO2 represents the concentration of oxidation saturation, and % HbA1c represents the concentration of glycated hemoglobin. In an embodiment, $f_1$ and $f_2$ may each correspond to the results of machine learning.

The non-invasive glycated hemoglobin or blood glucose measurement system 100 according to an embodiment of the present disclosure may measure the concentration of glycated hemoglobin (HbA1c) non-invasively using the Monte Carlo simulation (MCS), and this allows model approximation to avoid modeling into a homogeneous medium.

In other words, the non-invasive glycated hemoglobin or blood glucose measurement system 100 according to an embodiment of the present disclosure may dynamically simulate photons to predict the influence of interaction with media materials and enable accurate and easy non-invasive measurement of glycated hemoglobin by deriving the relationship between the intensity of light at three different wavelengths and the concentration of glycated hemoglobin (HbA1c) and oxidation saturation (SpO2).

Hereinbefore, although preferred embodiments of the present disclosure have been illustrated and described, it will be appreciated by those skilled in the pertinent technical field that various modifications and variations may be made without departing from the scope and spirit of the present disclosure as described in the claims below.

DESCRIPTION OF REFERENCE NUMERALS

100: Non-invasive glycated hemoglobin or blood glucose measurement system
410: Bones
420: Ligaments and tendons
430: Muscle
440: Fat
450: Skin
510: LED module
511: First LED module
512: Second LED module
513: Third LED module
520: Light detection unit

What is claimed is:

1. A non-invasive glycated hemoglobin or blood glucose measurement method which uses a Monte Carlo simulation, the method comprising:
   acquiring a two-dimensional scan image of a specific body part of a subject, wherein the two-dimensional scan image comprises either an MRI image or a CT image for the specific body part;
   generating a virtual three-dimensional model corresponding to the specific body part by using the two-dimensional scan image;
   performing the Monte Carlo simulation (MCS) on the three-dimensional model by:
   irradiating the three-dimensional model with virtual first to third incident lights having different wavelength values toward through virtual first to third LED modules positioned on one side of the three-dimensional model;
   and detecting virtual first to third derived lights derived from the first to third incident lights via the three-dimensional model through a virtual light detection unit positioned corresponding to the first to third LED modules;
   measuring photoplethysmography (PPG) signals using the MCS;
   calculating an AC-DC ratio equation using the photoplethysmography (PPG) signals measured according to the Monte Carlo simulation;
   constructing a machine learning mathematical model for glycated hemoglobin or blood glucose measurement using the AC-DC ratio equation, the machine learning mathematical model configured to output (1) a concentration of glycated hemoglobin (HbA1c) or blood glucose and (2) a concentration of oxygen saturation (SpO2); and
   using the machine learning mathematical model to calculate (1) the concentration of glycated hemoglobin (HbAlc) or blood glucose and (2) the concentration of oxygen saturation (SpO2) from an actual PPG signal measurement of the subject.

2. The method of claim 1, the specific body part comprises a part where capillaries existing under the skin are able to be sensed depending on a thickness of the skin.

3. The method of claim 1, wherein the generation of the three-dimensional model comprises generating the three-dimensional model by applying a 3D conversion algorithm to the two-dimensional scan image.

4. The method of claim 1, wherein the light detection unit is positioned at an opposite point or on the same side surface relative to positions of the first to third LED modules.

5. The method of claim 1, wherein the performance of the Monte Carlo simulation comprises simulating each movement of the incident light and the derived light as a result of applying Monte Carlo rules to virtual photons.

6. The method of claim 5, wherein the Monte Carlo rule comprises a traversing rule regarding at least one of reflection, transmission, or absorption according to collision between a specific photon and a specific medium.

7. The method of claim 1, wherein the calculation of the AC-DC ratio equation comprises calculating ratio equations for different wavelength values based on amplitude of the photoplethysmography (PPG) signals.

8. The method of claim 7, wherein the calculation of the AC-DC ratio equation comprises applying each derived light of first and second derived light sets composed of two of the first to third derived lights to the AC-DC ratio equation regarding the different wavelength values to generate first and second AC-DC ratio equations.

9. The method of claim 7, wherein the construction of the mathematical model comprises constructing a mathematical model between a value of the AC-DC ratio equation and each value of glycated hemoglobin (HbA1c) or blood glucose and oxidation saturation (SpO2) predefined corresponding to a reference photoplethysmography signal.

10. The method of claim 8, wherein the construction of the machine learning mathematical model comprises constructing a machine learning mathematical model between values of each of the first and second AC-DC ratio equations and each value of glycated hemoglobin (HbA1c) or blood glucose and oxidation saturation (SpO2) predefined.

11. The method of claim 1, wherein the construction of the machine learning mathematical model comprises calibrating the machine learning mathematical model based on actual values of the glycated hemoglobin (HbA1c) or blood glucose and the oxidation saturation (SpO2) measured from the measurement subject to be measured.

12. A non-invasive glycated hemoglobin or blood glucose measurement system which uses a Monte Carlo simulation, the system comprising:
   a processor that includes the following units:
   a 3D modeling unit that acquires a two-dimensional scan image of a specific body part of a subject and generates a virtual three-dimensional model corresponding to the specific body part by using the two-dimensional scan image, wherein the two-dimensional scan image comprises either an MRI image or a CT image for the specific body part;
   a simulation performance unit that performs the Monte Carlo simulation (MCS) on the basis of the three-dimensional model by:
   irradiating the three-dimensional model with virtual first to third incident lights having different wavelength values toward through virtual first to third LED modules positioned on one side of the three-dimensional model;
   and detecting virtual first to third derived lights derived from the first to third incident lights via the three-dimensional model through a virtual light detection unit positioned corresponding to the first to third LED modules;
   measuring photoplethysmography (PPG) signals using the MCS;
   a measurement model construction unit that calculates a AC-DC ratio equation using the photoplethysmography (PPG) signals measured according to the Monte Carlo simulation and constructs a machine learning mathematical model for glycated hemoglobin or blood glucose measurement using the AC-DC ratio equation, the machine learning mathematical model configured to output (1) a concentration of glycated hemoglobin (HbA1c) or blood glucose and (2) a concentration of oxygen saturation (SpO2); and
   a concentration calculation unit that uses the machine learning mathematical model to calculate (1) the concentration of glycated hemoglobin (HbA1c) or blood glucose and (2) the concentration of oxygen saturation (SpO2) from an actual PPG signal measurement of the subject.

* * * * *